(12) United States Patent
Kelson et al.

(10) Patent No.: US 9,243,206 B2
(45) Date of Patent: *Jan. 26, 2016

(54) MICRO-SPIKE ALGAE HARVESTING AND BIOFUEL EXTRACTION SYSTEM AND METHOD THEREFOR

(71) Applicants: John Kelson, San Diego, CA (US); Benjamin J. Pavlik, Oakland, CA (US)

(72) Inventors: John Kelson, San Diego, CA (US); Benjamin J. Pavlik, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/608,082

(22) Filed: Jan. 28, 2015

(65) Prior Publication Data

US 2015/0141681 A1    May 21, 2015

Related U.S. Application Data

(63) Continuation of application No. 13/458,814, filed on Apr. 27, 2012, now Pat. No. 8,960,582.

(60) Provisional application No. 61/479,735, filed on Apr. 27, 2011.

(51) Int. Cl.
| | |
|---|---|
| *C11B 1/10* | (2006.01) |
| *B02C 19/00* | (2006.01) |
| *C12M 1/00* | (2006.01) |
| *C12M 1/26* | (2006.01) |
| *B01D 43/00* | (2006.01) |

(52) U.S. Cl.
CPC . *C11B 1/10* (2013.01); *B01D 43/00* (2013.01); *B02C 19/00* (2013.01); *C12M 1/00* (2013.01); *C12M 21/02* (2013.01); *C12M 33/00* (2013.01); *C12M 47/06* (2013.01)

(58) Field of Classification Search
CPC ........ B02C 23/00; B02C 19/00; C12M 33/00; C12M 1/00; C12N 1/12; C11B 1/10; B01D 43/00
USPC ....................................... 241/2, 274
See application file for complete search history.

(56) References Cited

U.S. PATENT DOCUMENTS

| | | | | |
|---|---|---|---|---|
| 5,975,447 | A * | 11/1999 | Brusseau | 241/95 |
| 8,043,496 | B1 * | 10/2011 | Schuh et al. | 210/121 |
| 8,789,782 | B1 * | 7/2014 | Blume et al. | 241/95 |
| 8,960,582 | B2 * | 2/2015 | Kelson et al. | 241/274 |
| 2010/0206174 | A1 * | 8/2010 | Loden | 99/275 |

* cited by examiner

*Primary Examiner* — Faye Francis
(74) *Attorney, Agent, or Firm* — Beeson Skinner Beverly, LLP

(57) ABSTRACT

A micro-spike algae harvesting and biofuel extraction system and method therefor whereby an algal solution is dispersed from a selected height onto an inclined micro-spike board which forms a substrate for supporting an array of upwardly-extending miniature spikes, wherein the miniature spikes puncture algae cells suspended in the solution to release biofuel contained therein.

16 Claims, 5 Drawing Sheets

MICRO-SPIKE ALGAE HARVESTING AND BIOFUEL EXTRACTION SYSTEM AND METHOD THEREFOR

CROSS-REFERENCE TO RELATED APPLICATIONS

This is a continuation of application Ser. No. 13/458,814, filed Apr. 27, 2012, issued on Feb. 24, 2015 as U.S. Pat. No. 8,960,582, which claims the benefit of U.S. Provisional Application 61/479,735, filed Apr. 27, 2011.

BACKGROUND OF THE INVENTION

1. Field of the Invention

This invention relates generally to systems and methods for harvesting biofuel from algae, and particularly to a system and method for extracting biofuel from algae cells in an algal solution using an array of miniature spikes mounted on an inclined micro-spike board.

2. Discussion of the Prior Art

One of the challenges involved in harvesting oil from algae involves finding an efficient technology for rupturing the algae's outer cell membrane in order to extract the oil contained within the algae cell. Considerable efforts have been dedicated to efficient cell lysis, as discussed below, but the technologies which have been developed each have one or more disadvantages such as high energy costs, lengthy time requirements, expensive equipment, and low yield.

Harvesting

Known forms of harvesting algal cells fall into three general categories: biomass recovery, dewatering and drying. Specific technologies within each category are discussed below.

Biomass Recovery

Centrifugation uses equipment to spin the algal medium. The centrifugal force of the machine used causes dense material to move away from the spinning axis. This forces nearly all the water to flow outward and leaves a much higher concentration of algae in the medium, thus enabling the algae to be separated out since it is less dense than water. Centrifugation has several disadvantages. The equipment required for this process is fairly expensive. The equipment also consumes a lot of energy since the centrifuge must run at hundreds, if not thousands, of RPMs for an extended amount of time. Finally, the intense use of energy diminishes the net energy balance upon arrival at the crude biodiesel stage. For purposes of this disclosure Net Energy Balance is equal to the Final Energy Output minus Process-related Energy Inputs.

Decantation is a method of separating mixtures. The process involves pouring a solution from one container into another. If done correctly the algae can be separated from most of the water and any sediment in the solution. The primary disadvantage of decantation is that it involves fairly expensive equipment. While decantation has lower energy requirements than centrifugation, most decanters are used in combination with a centrifuge.

Flocculation involves one of several means for bringing colloidal objects in a mixture out of suspension in the form of flakes or lumps.

Autoflocculation causes the algae to flocculate and form "lumps" by stopping the supply of carbon dioxide to the algae. One disadvantage is that autoflocculation usually requires some extra equipment, but it is fairly inexpensive. However, this routine can take a fairly long time.

Bioflocculation uses organic material to cause the algae to group together and form lumps. For example, chitosan, a linear polysaccharide derived from shellfish, is often used. A secondary process is required to filter the chitosan out of the algae before it reaches the crude biofuel stage. This secondary stage requires additional costs for machinery and energy. In addition, chitosan can be expensive.

Chemical flocculation is a method which separates algae from water by using chemicals. The main disadvantage of chemical flocculation is that the chemicals required are very expensive. In addition, since the chemicals used in the process usually bond to the algae in one form or another, the algae must be separated from the chemical flocculants. Removing these chemicals is expensive and time consuming. Also, many known flocculants like ferric chloride, which is commonly used in the industry, can be very harmful to the environment and are frowned upon by most organizations involved in the creation of biofuels. Ferric chloride is fairly toxic and known to cause harm to the environment.

Froth flotation is another method of separating algae from its growth solution. This process achieves separation by increasing the pH of the solution and bubbling air into the solution along with a basic chemical. Eventually, this causes the algae cells to aggregate in a foam or froth at the surface of the solution. Although the equipment needed is not very expensive, the basic chemicals can be expensive depending on which ones are used. In addition, secondary equipment is needed to treat the post-process solution since it cannot be released into the environment with the elevated pH resulting from the method.

Microfiltration is a process in which the algal solution is pumped through a micro-fabricated filter or forced through a membrane. The algae cells gather on one side of the filter or membrane, while the smaller water molecules pass through into a separate tank. This process can be somewhat expensive and its usefulness is limited since it only segregates the algae. The algae still must be lysed so that the oils may be released to form biofuel.

Dewatering

One method of dewatering is to use a draining tank to remove the algae from the solution through a slow cycle of filtering and pumping. This is done by pumping the solution into a tank and then draining the water from the bottom of the tank. This method can be inexpensive, but it is very inefficient.

Once algae has been separated from most of the solution it can be further dewatered using a mechanical press. An apt mechanical press is a lot like a giant vice such as a screw, expeller or piston. The algae is then put under pressure for several hours and often attains very low water content after this process. The primary disadvantages of this method are that it is very time consuming and produces low yields.

Drying

There are numerous techniques for drying out algae. Drum drying is a method used for drying out algae into a film or paste using a large rotating drum that slowly applies heat. The dried algae film or paste is then scraped off the drum surface. Rotary drying is much like drum drying except that an air pump is used to alter the pressure in order to evaporate water. Freeze drying is a dehydration process which works by freezing the subject material and then reducing the surrounding pressure and adding enough heat to allow the frozen water in the material to sublime directly from the solid phase to the gas phase. Solar drying uses glass and lenses to focus and trap heat from the sun. Spray drying is a method of producing a dry powder from a liquid or slurry by rapidly drying with a hot gas. Spray drying is the preferred method of drying of many thermally-sensitive organic materials such as algae.

Most of the drying processes require expensive equipment and use high amounts of energy which has a significant negative impact on the Net Energy Balance. The only exception to this is solar drying which takes an extremely long time and its practical use is limited to very small batches.

Extraction

After the algae have been harvested, oil may be extracted from the algae in the following ways.

Ultrasonic-assisted extraction uses sonochemistry to assist with the extraction of algal oil. Most equipment uses an ultrasonic reactor. The process uses ultrasonic waves to generate bubbles. These bubbles are usually created within a solvent. Once created the bubbles collapse and create small shock waves that break the cell wall. The material inside of the algae cell will spread out into the solvent. The major disadvantage of ultrasonic-assisted extraction is extremely high equipment and maintenance costs. Moreover, the solvents used must be filtered out of the solution resulting in additional costs. The Net Energy Balance is severely impacted by this method.

Mechanical expulsion is the act of extracting oil from algae through a special press or piston operated machine. This process can be very time consuming and has a limited capacity.

Solvent extraction is a process not unlike flocculation, where a solvent is mixed into the algal mass. The chemicals used perforate the cell wall and bind to the triglycerides (oil) within the algae cell. Suitable chemicals for the process include benzene, hexane, and petroleum ether. A serious disadvantage with solvent extraction is that many of the chemicals used can be extremely toxic and care must be taken to avoid exposure to vapors or direct contact with the skin, either of which can result in serious physical problems. Benzene, for example, is classified as a carcinogen. Some of these chemicals are also very expensive.

Supercritical fluid extraction is the process of separating one component (the extractant) from another (the matrix) using a supercritical fluid such as $CO_2$ as the extracting solvent. This method liquefies $CO_2$ using various chemicals and requires extremely high pressure. Heat is then applied until the elements within the solution reach a liquid or gas state. The $CO_2$ is then added, to extract the oil from the algae's cell. Although, this is one of the most efficient means to extract oil from algae, the process needs specialized equipment, most of which is very expensive and energy intensive.

Enzymatic extraction uses enzymes to degrade the cell walls with water acting as the solvent. Through enzymatic extraction, the algal solution is mixed with enzymes to weaken the wall all of the cell. In this process water acts as the solvent. The primary disadvantage of enzymatic extraction is that the high cost of producing and then filtering out the enzymes makes this method unrealistic with the present technology.

Sonication, or ultrasonic extraction, is a technique which uses ultra-low and ultra-high sound waves to generate bubbles within the algal solution. These alternating frequencies cause the bubbles to burst which rupture the cell walls, releasing the oil within. The disadvantage of sonication is that equipment is very expensive and needs much more maintenance than other forms of extraction.

Osmotic shock, also known as osmotic stress, is a method that induces a sudden change in the osmotic pressure around the algae cell. Usually achieved through the addition of a salt, the cells membrane weakens and eventually breaks down due to osmotic pressure shifts. By breaking down the membrane, the oil is released from the cell. Very few organizations have achieved a working model of this process, and success has been achieved with a very few unique strains of algae. At this time it is thought to be an unrealistic method of extraction for oil producing algae.

In view of the state of the art, there is a need for a simple, inexpensive, and energy efficient mechanism for harvesting biofuel from algae cells.

BRIEF DESCRIPTION OF THE ILLUSTRATIONS

DETAILED DESCRIPTION OF THE ILLUSTRATED EMBODIMENT

Figure 1:
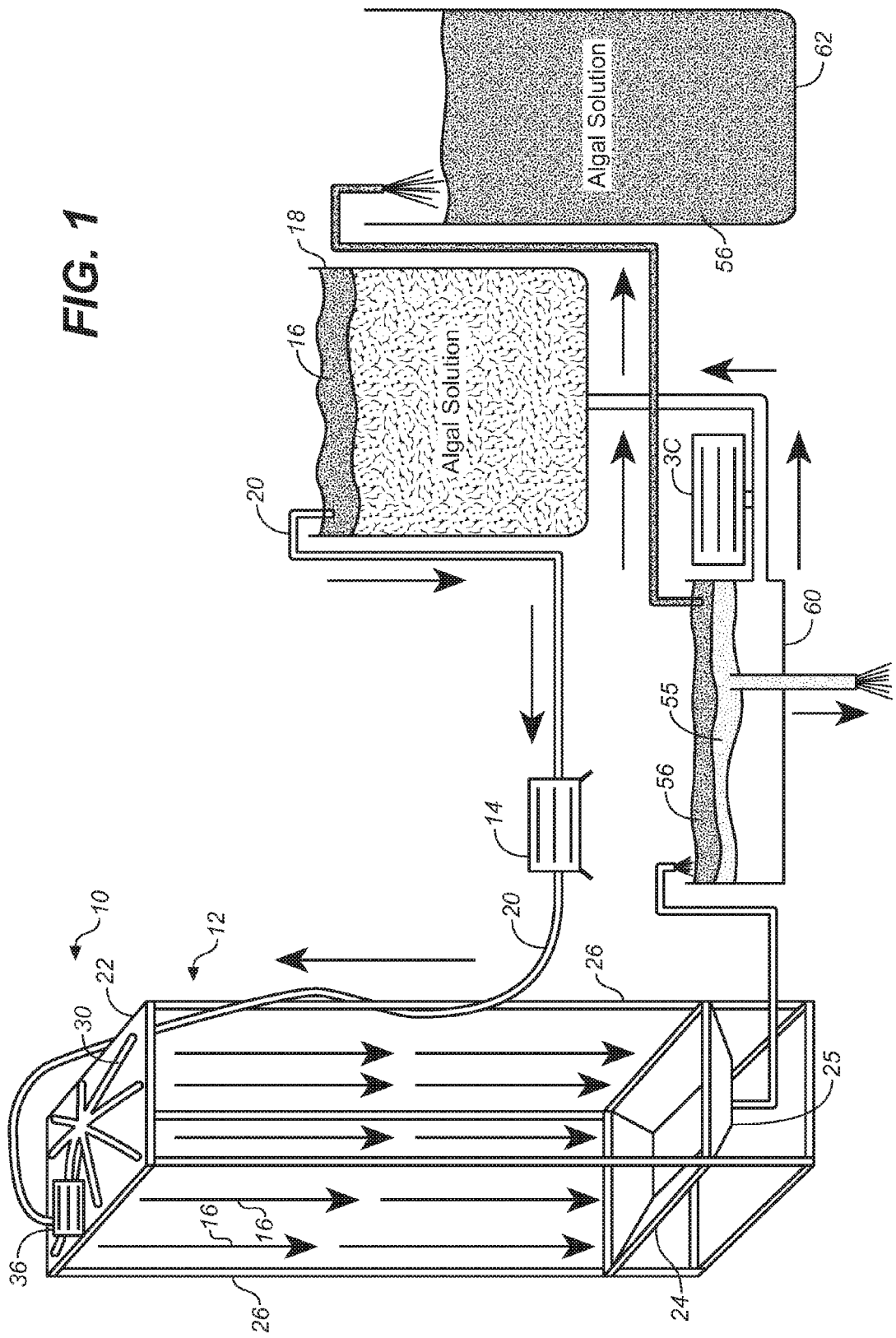
FIG. 1 is a schematic diagram of the components of a micro-spike algae harvesting system according to the invention.

With reference to the drawings, a micro-spike algae harvesting system 10 according to the invention is shown in FIG. 1. The system 10 comprises an enclosed vertical tower 12, a pump 14 for delivering algal solution 16 from a reservoir 18 to the tower 12 through tubing, hose or conduit 20. A sprinkling system 22 on the top of the tower disperses and showers an algal solution of algae cells and water from a height onto a micro-spike board 24 at the bottom of the tower 12. The tower 12 is constructed of a rigid framework 26 which provides support for the sprinkling system 22 and the micro-spike board 24. The tower 12 may be fabricated from metal or other suitable materials. In a simple system, the tower 12 may be sealed in plastic, but more permanent wall-type enclosures are contemplated to be encompassed within the invention. In one embodiment, the height of the tower 12 will be approximately thirty feet, but there may be adjustments in the precise height depending on the algal species involved and the characteristics of the sprinkling system 22. It is anticipated that the height of the sprinkling system 22 above the micro-spike board 24 will be between approximately twenty to thirty feet depending on the algal strain being processed and other characteristics of the system.

Figure 2A:
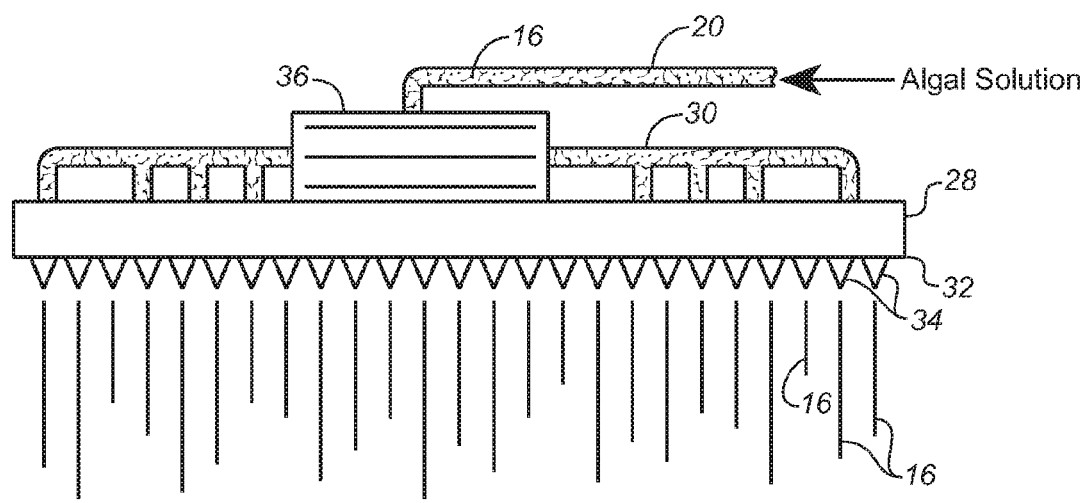
FIGS. 2A and 2B are elevation views of a drip-type sprinkling system and a spray-type sprinkling system, respectively.
Figure 2B:
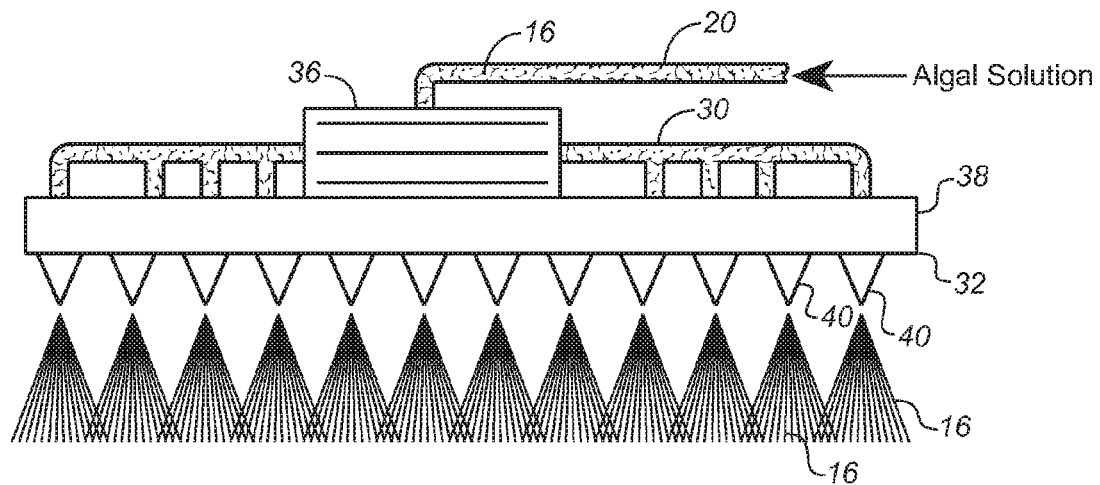
Figure 3A:
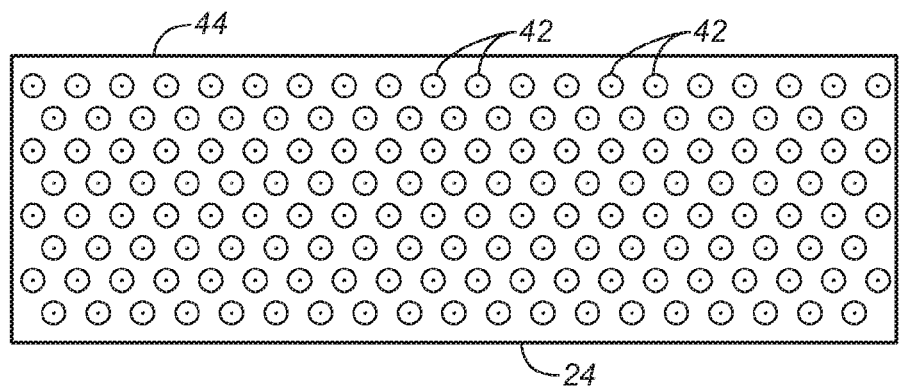
FIG. 3A is a plan view of a simplified diagram of a micro-spike board.
Figure 4:
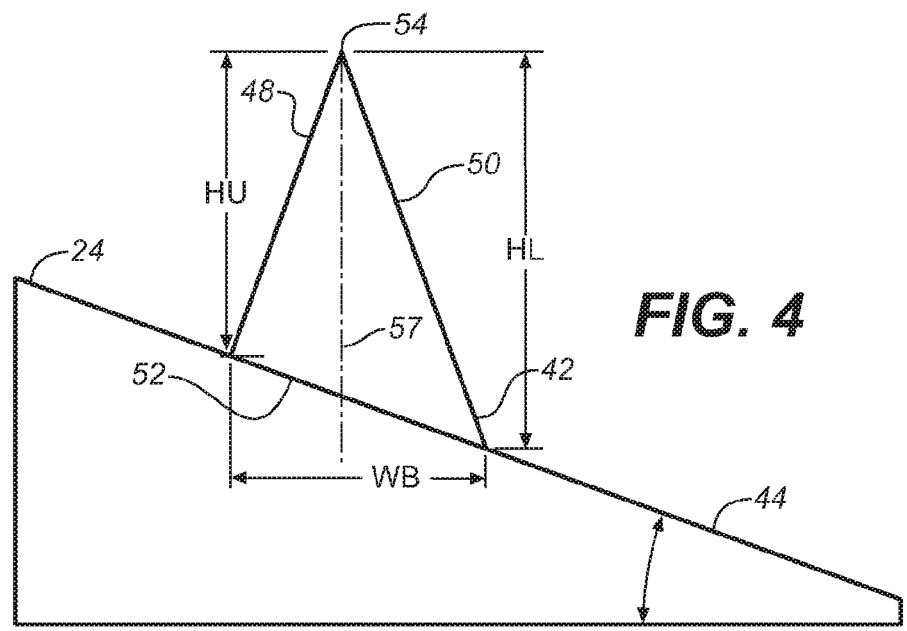
FIG. 4 is an enlarged schematic view of a single spike on a micro-spike board.
Figure 5:
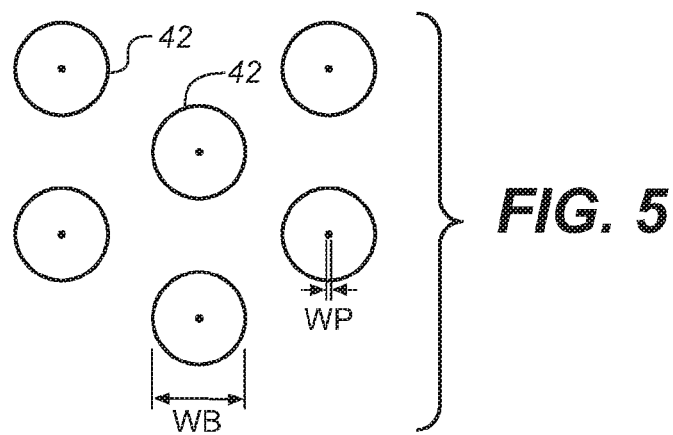
FIG. 5 is a top plan view of a portion of a micro-spike board.
Figure 3B:
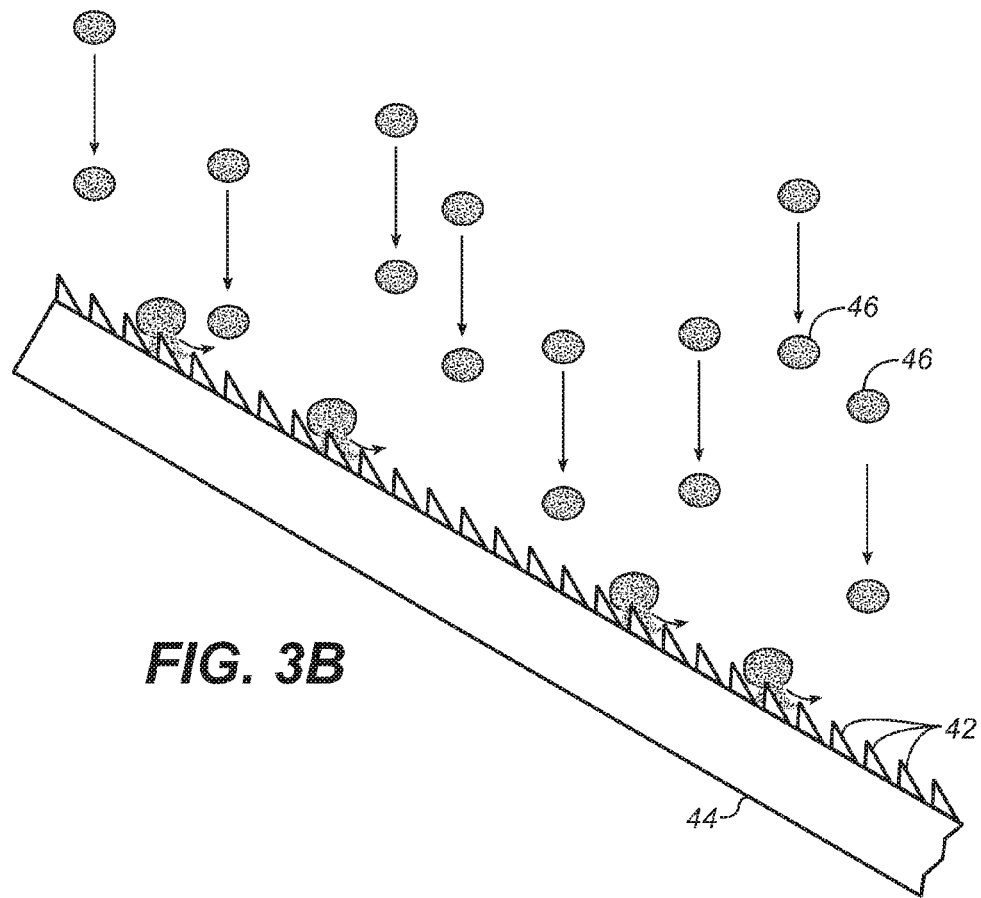
FIG. 3B is an elevation view of the micro-spike board shown in FIG. 3A set at an angle, and showing individual algae cells falling into the micro-spike board.
Figure 3C:
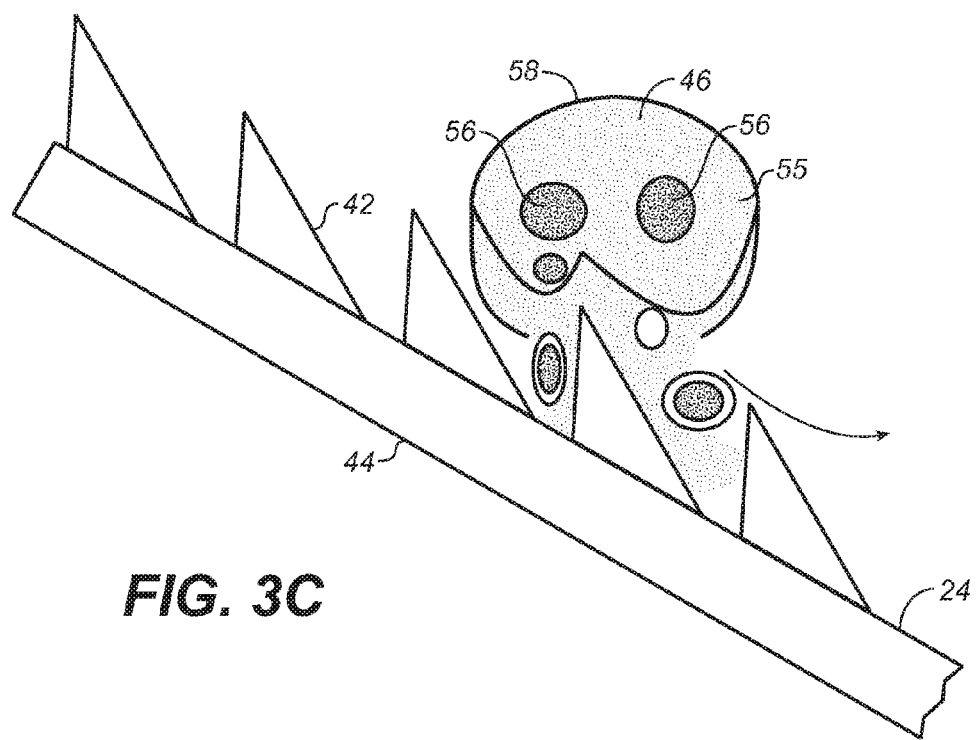
FIG. 3C is an enlarged view of the micro-spike board shown in FIGS. 3A and 3B showing an algae cell being ruptured on one of the spikes on the micro-spike board.
Figure 6A:
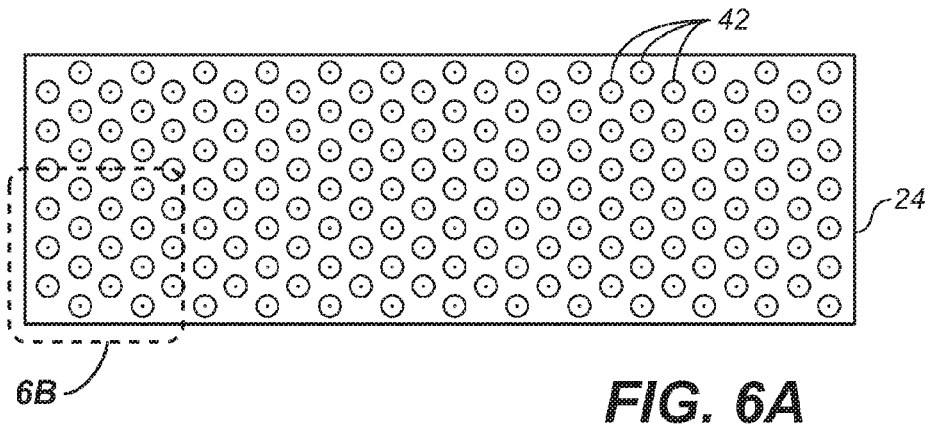
FIG. 6A is a top plan view of a representative embodiment of a micro-spike board showing the micro-spikes arrayed in a hexagonal pattern.
Figure 6B:
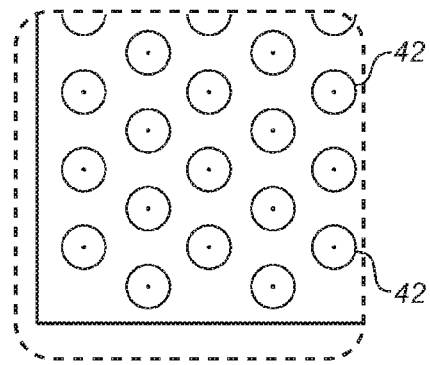
FIG. 6B is a close-up top plan view of a portion of the micro-spike board shown in FIG. 6A.
Figure 7A:
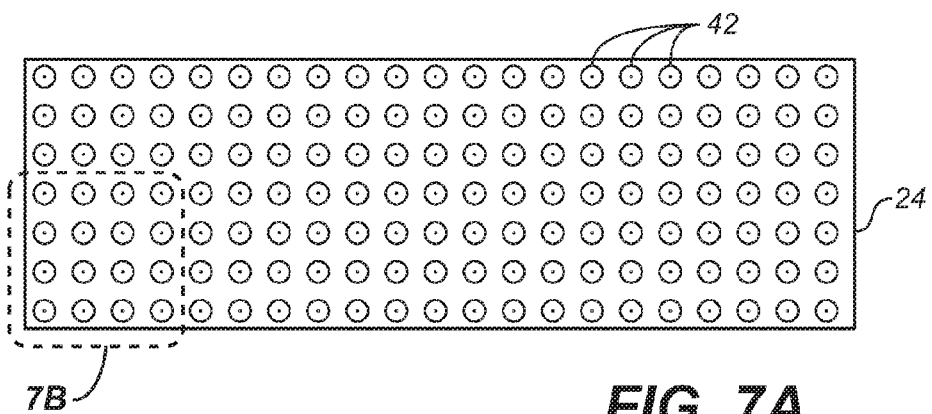
FIG. 7A is a top plan view of a representative embodiment of a micro-spike board showing the micro-spikes arrayed in parallel rows.
Figure 7B:
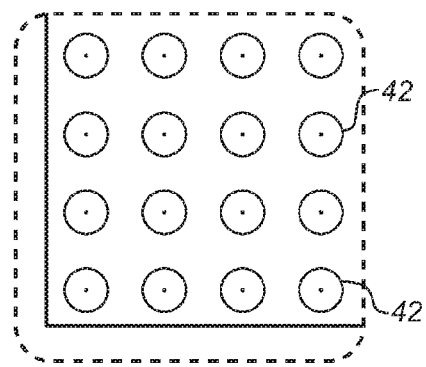
FIG. 7B is a close-up top plan view of a portion of the micro-spike board shown in FIG. 7A.

The sprinkling system 22 may consist of a drip system 28 shown in FIG. 2A, or a spraying system 38 shown in FIG. 2B. The drip system 28 comprises a plurality of tubes, hoses or other suitable conduits 30 to disperse the solution 16 broadly across a backing plate 32 from which a plurality of drip nozzles 34 depend. The drip system 28 disperses the solution and relies on gravity to drip feed the solution 16 onto the micro-spike board 24. An auxiliary pump 36 may assist in distributing solution 16 received from the reservoir 18 to the plurality of dispersive conduits 30.

The spraying system 38 shown in FIG. 2B is similar to the drip system 28 except that instead of drip nozzles 34, a plurality of spray nozzles 40 depend from backing plate 32. Higher pressure is developed in the conduit 30 to force the algal solution 16 out of the spray nozzles 40 faster than compared to the drip nozzles 34. The selection of whether to use a drip system 28 or spray system 38 may affect the height that the sprinkling system 22 is suspended above the micro-spike board 24.

FIG. 3A shows an overhead close-up view of a portion of one embodiment of a micro-spike board 24 according to the invention, the board 24 including an array of miniature spikes 42 supported on a substrate 44. Each of the spikes 42 is fixed on the board 24 at an angle such that when the board is set at a slope, as shown in FIG. 3B, the spikes 42 are pointed generally upward. While in the embodiments illustrated in FIGS. 3A and 3B, the spikes are pointed slightly more towards the upper end of the board relative to a true vertical orientation, it will be understood by those of skill in the art that the precise angle at which the spikes are pointed may vary depending on the species of algae being processed, the viscosity of the algal solution, and other system variables. In one embodiment of the invention, board 24 has dimensions of three feet by three feet and is set at an angle A of between fifteen and thirty degrees relative to horizontal. It will be understood by those of skill in the art that the size of the board and the precise angle at which it is set to operate may vary according to the species of algae being processed and other characteristics of the system 10.

As algal solution 16 drips or is sprayed from the sprinkling system 22 as shown in FIG. 1, individual algae cells 46 fall onto the micro-spike board 24 where they are punctured by the micro-spikes 42. See FIG. 3B. FIG. 30 shows a close-up view of an algae cell 46 being punctured by one of the spikes 42 on the micro-spike board 24.

With reference now to FIGS. 4 and 5, each spike 42 has a conically shaped geometric configuration and is characterized by an upper side 48, a lower side 50, a base 52, a point 54 at the apex, and a central axis 57. Each spike 42 is fixed angularly on the substrate 44 which disposes the axis 57 relative to the substrate at an angle of between approximately 60 and 75 degrees. In one embodiment, each spike forms an oblique cone.

The spike size will vary depending on the algal strain being processed and the environment in which it was grown. Longer spikes may be required for use with algal solutions having high salinity or mineral concentrations which can increase the buoyancy of the algae. The height HU of the upper side 48, measured from the substrate 44, varies from one embodiment to another from between approximately 15 and approximately 100 micrometers, the height HL of the lower side 50 varies from between approximately 17 to approximately 100 micrometers, the horizontal width WB of the base 52 varies between approximately 10 and approximately 71 micrometers, and the width WP of the point 54 varies from between approximately 0.2 to approximately 4 micrometers. In one embodiment, the upper side 48 has a height of 15 micrometers, the lower side 50 has a height of 17 micrometers, the base 52 has a width of 10 micrometers, and the point 54 has a width of 0.2 micrometers. The dimensions of this embodiment and three other embodiments are set forth in the following table:

| Embodiment | Height of upper side | Height of lower side | Width of base | Width of point |
|---|---|---|---|---|
| 1 | 15 | 17 | 10 | 0.2 |
| 2 | 30 | 34 | 25 | .5 |
| 3 | 60 | 70 | 50 | 1 |
| 4 | 90 | 100 | 71 | 2 |

The spikes 42 may be manufactured by micro-etching the substrate 44. Using known micro-etching techniques, it is estimated that the point 54 of each spike will have a width varying from approximately 0.2 to approximately 4 micrometers. Ideally, each micro-spike 42 will have concave sides. The point 54 will need to be much narrower than the base 52 to ensure that all algae cells 46 making contact with it are punctured sufficiently to release the oil 56 residing within the algae's outer cell membrane 58.

The micro-spikes 42 may be arrayed on the substrate 44 in numerous different patterns. FIG. 6A shows a micro-spike board 24 on which the micro-spikes 42 are arranged in a hexagonal pattern in which each row is offset from the immediately adjoining rows. FIG. 6B is a close-up view of the hexagonal arrangement of the spikes 42 shown in FIG. 6A. FIG. 7A shows a micro-spike board 24 on which the micro-spikes 42 are arranged in a series of rows parallel in both dimensions on the board 24. FIG. 7B is a close-up view of the parallel arrangement of the spikes 42 shown in FIG. 7A. Those of skill in the art will recognize that the spikes 42 may be arranged in other patterns depending on proven efficiency and cost.

Referring again to FIG. 1, algal solution 16 is pumped from reservoir 18 via conduit 20 to the sprinkling system 22 on top of the tower 12. The sprinkling system 22 disperses the solution 16 and drips or sprays it from a height of twenty to thirty feet above onto micro-spike board 24. As the algae cells 46 in the solution 16 impact and slide along the board 24, the upwardly extending micro-spikes 42 puncture the algae cells 46 and release chlorophyll and protein matter 55 and oil 56 therein. Although not illustrated, air dryers or fans may be installed adjacent to the board 24 to help keep it clean and remove any cellular mass buildup. The solution 16 slides off the slanted board 24 and into a holding tank 25 from which it is pumped into a churning tank 60. Agitation in the churning tank 60 causes the oil 56 to rise to the top of the tank from which it can be pumped into an oil holding tank 62. Water and undamaged algae cells are pumped back into the original reservoir 16 to repeat the process. The chlorophyll and protein matter 55 is collected for other uses. The crude oil 56 collected in this process can be refined into virtually any fuel form or polymer currently produced in the hydrocarbon industry.

One simple embodiment of the system comprises (A) two spraying units, and/or a drip system, (B) two to three water pumps, (C) four air dryers/fans (3 feet×3 feet), (D) approximately 100 feet of hose(s) for pumping, (E) a metal framework, sealed possibly in plastic, forming a tower roughly 30 feet high which will provide structural support for all equipment, (F) three 100 gallon tanks, and (G) one board of micro-fabricated spikes measuring approximately 3 feet×3 feet (set at an angle of 15 to 30 degrees).

A micro-spike algae harvesting system has the substantial advantage that it relies on gravity and a simple sprinkling system attached to a pump. Most existing methods for harvesting algae and algae cell lysis involve much more use of energy by, for example, spinning the algae at hundreds if not thousands of RPMs in a centrifugation process. The invention also interacts with the algae cells on a much smaller level than most other processes and integrates the harvesting and extraction phases into a seamless method of producing biofuel.

There have thus been described certain preferred embodiments of a micro-spike algae harvesting and biofuel extraction system and method. While preferred embodiments have been described and disclosed, it will be recognized by those with skill in the art that modifications are within the true spirit and scope of the invention. The appended claims are intended to cover all such modifications.

What is claimed is:

1. A method for extracting biofuel from algae comprising: holding a planar substrate at an inclined angle,
dispersing a solution of algae cells from a selected height above said planar substrate onto an array of conically shaped miniature spikes extending upwardly from said planar substrate,
puncturing said algae cells with said array of miniature spikes, and
releasing biofuel contained in said algae cells.

2. The method for extracting biofuel from algae of claim 1 comprising:
dispersing said solution onto said array of miniature spikes from a height of between twenty and thirty feet above said planar substrate.

3. The method for extracting biofuel from algae of claim 1 wherein:
the center axis of each spike of said array of spikes is disposed at a selected angle relative to said planar substrate of between approximately 60 and approximately 75 degrees.

4. The method for extracting biofuel from algae of claim 1 further comprising:
orienting each spike in said array of spikes toward the upper end of said planar substrate.

5. The method for extracting biofuel from algae of claim 1 further comprising:
inclining said planar substrate relative to a horizontal plane at an angle between approximately 15 to 30 degrees.

6. The method for extracting biofuel from algae of claim 5 further comprising:
inclining the center axis of each spike of said array of spikes at an angle relative to said planar substrate of between approximately 60 and 75 degrees.

7. The method for extracting biofuel from algae of claim 1 wherein:
each spike of said array of spikes forms the shape of an oblique cone relative to said planar substrate.

8. The method for extracting biofuel from algae of claim 1 wherein:
each said spike of said array of miniature spikes has an apex, an upper side, a lower side, and a base, said upper side extending from said apex to said planar substrate at an upper intersection point a distance of between approximately 15 and 90 micrometers, said lower side extending opposite said upper side from said apex to said substrate at a lower intersection point, said lower intersection point disposed below said upper intersection point, and said base having a width extending between said upper and lower intersection points of between approximately 10 and 71 micrometers.

9. The method for extracting biofuel from algae of claim 8 wherein:
the apex of each spike of said array of miniature spikes includes a point having a width between approximately 0.2 micrometers to approximately 4.0 micrometers.

10. The method for extracting biofuel from algae of claim 1 further comprising:
dispersing said solution by dripping it onto said array of miniature spikes.

11. The method for extracting biofuel from algae of claim 1 further comprising:
dispersing said solution by spraying it under pressure onto said array of miniature spikes.

12. The method for extracting biofuel from algae of claim 1 further comprising:
catching said solution and said released biofuel that slides off of said inclined planar substrate.

13. The method for extracting biofuel from algae of claim 1 further comprising:
manufacturing said planar substrate by micro-etching.

14. The method for extracting biofuel from algae of claim 1 further comprising:
pumping the algal solution into a churning tank,
churning said solution,
separating said biofuel from said algal solution, and
pumping said biofuel into a holding tank.

15. A method for extracting biofuel from algae comprising:
holding a planar substrate at an inclined angle of between approximately 15 to 30 degrees relative to a horizontal plane,
dispersing an algal solution of algae cells from a height of between twenty and thirty feet above said planar substrate onto an array of conically shaped miniature spikes extending upwardly from said planar substrate,
each said spike of said array of miniature spikes having an apex, an upper side, a lower side, and a base, said upper side extending from said apex to said planar substrate at an upper intersection point a distance of between approximately 15 and 90 micrometers, said lower side extending opposite said upper side from said apex to said substrate at a lower intersection point, said lower intersection point disposed below said upper intersection point, and said base having a width extending between said upper and lower intersection points of between approximately 10 and 71 micrometers
the center axis of each spike of said array of spikes inclined at an angle relative to said planar substrate of between approximately 60 and 75 degrees, puncturing said algae cells with said array of miniature spikes,
releasing biofuel contained in said algae cells, and
catching said algal solution and said released biofuel that slides off of said inclined planar substrate.

16. A micro-spike algae harvesting and biofuel extraction system comprising:
a planar substrate held at an inclined angle relative to a horizontal plane of between approximately 15 and 30 degrees,
an array of miniature spikes supported on said substrate, each spike of said array of spikes having a conic shape, each spike fixed on said substrate at a selected angle such that each spike is pointed upward, and
a sprinkling system for dispersing an algal solution of algae cells from a selected height above said planar substrate onto said array of miniature spikes for puncturing said algae cells to release biofuel contained therein.

* * * * *